(12) United States Patent
Mujwid et al.

(10) Patent No.: US 8,562,628 B2
(45) Date of Patent: Oct. 22, 2013

(54) LINEAR MOTION DELIVERY SYSTEM FOR FEMALE STERILIZATION DEVICE

(75) Inventors: James Ryan Mujwid, Crystal, MN (US); Kevin R. Arnal, Excelsior, MN (US)

(73) Assignee: Conceptus, Inc., Mountain View, CA (US)

( * ) Notice: Subject to any disclaimer, the term of this patent is extended or adjusted under 35 U.S.C. 154(b) by 1189 days.

(21) Appl. No.: 11/695,887

(22) Filed: Apr. 3, 2007

(65) Prior Publication Data

US 2007/0244439 A1     Oct. 18, 2007

Related U.S. Application Data

(60) Provisional application No. 60/744,178, filed on Apr. 3, 2006.

(51) Int. Cl.
*A61D 1/06* (2006.01)
*A61M 29/00* (2006.01)
*A61F 2/06* (2013.01)

(52) U.S. Cl.
USPC .......................... 606/135; 606/200; 623/1.11

(58) Field of Classification Search
USPC ................ 606/135, 193, 200; 623/1.11, 1.12, 623/1.23; 128/831, 843
See application file for complete search history.

(56) References Cited

U.S. PATENT DOCUMENTS

| | | | |
|---|---|---|---|
| 2,309,502 A | * | 1/1943 | Douglas ........................ 604/135 |
| 2,578,812 A | * | 12/1951 | Kollsman ...................... 604/117 |
| 2,830,586 A | * | 4/1958 | Dann et al. ................... 604/220 |
| 3,334,629 A | | 8/1967 | Cohn |
| 3,687,129 A | | 8/1972 | Nuwayser |
| 4,140,126 A | | 2/1979 | Choudhury |

(Continued)

FOREIGN PATENT DOCUMENTS

| | | |
|---|---|---|
| AU | 707047 | 7/1999 |
| AU | 739429 | 10/2001 |

(Continued)

OTHER PUBLICATIONS

A. Thurmond, MD, "Transcervical Fallopian Tube Catheterization," Seminars in Interventional Radiology, vol. 9 (No. 2), p. 80-86 (Jun. 1992).

(Continued)

*Primary Examiner* — Gary Jackson
*Assistant Examiner* — Jonathan Hollm
(74) *Attorney, Agent, or Firm* — Blakely, Sokoloff, Taylor & Zafman LLP

(57) ABSTRACT

A delivery system for deploying an occlusion device comprises a piston having a threaded proximal end, an elongated delivery catheter having a proximal end, a distal end, and an inner lumen extending between the proximal and distal ends of the delivery catheter, and a drive mechanism comprising an internally threaded nut member and a spring member. The piston is moveable between a first axial position and a second axial position. The internally threaded nut member receives the threaded proximal end of the piston. The spring member, which is coupled to the internally threaded nut member, rotates the nut member to drive the piston from the first axial position toward the nut member to the second axial position. Driving the piston toward the nut member retracts the attached delivery catheter and deploys an occlusion device from within the inner lumen and through the distal end of the delivery catheter.

22 Claims, 14 Drawing Sheets

(56) References Cited

U.S. PATENT DOCUMENTS

| | | | |
|---|---|---|---|
| 4,246,896 A | 1/1981 | Horne et al. | |
| 4,503,569 A | 3/1985 | Dotter | |
| 4,562,596 A | 1/1986 | Kornberg | |
| 4,579,110 A | 4/1986 | Hamou | |
| 4,595,000 A | 6/1986 | Hamou | |
| 4,600,014 A * | 7/1986 | Beraha | 600/567 |
| 4,606,336 A | 8/1986 | Zeluff | |
| 4,700,701 A | 10/1987 | Montaldi | |
| 4,733,665 A | 3/1988 | Palmaz | |
| 4,869,268 A | 9/1989 | Yoon | |
| 4,964,850 A | 10/1990 | Bouton et al. | |
| 4,969,458 A | 11/1990 | Wiktor | |
| 4,994,069 A | 2/1991 | Ritchart et al. | |
| 5,108,420 A | 4/1992 | Marks | |
| 5,147,370 A | 9/1992 | McNamara et al. | |
| 5,176,692 A | 1/1993 | Wilk et al. | |
| 5,192,301 A | 3/1993 | Kamiya et al. | |
| 5,303,719 A | 4/1994 | Wilk et al. | |
| 5,382,261 A | 1/1995 | Palmaz | |
| 5,443,500 A | 8/1995 | Sigwart | |
| 5,456,713 A | 10/1995 | Chuter | |
| 5,474,089 A | 12/1995 | Waynant | |
| 5,499,995 A | 3/1996 | Teirstein | |
| 5,545,210 A | 8/1996 | Hess et al. | |
| 5,554,154 A * | 9/1996 | Rosenberg | 606/80 |
| 5,601,600 A | 2/1997 | Ton | |
| 5,935,137 A | 8/1999 | Saadat et al. | |
| 6,090,063 A | 7/2000 | Makower et al. | |
| 6,096,052 A | 8/2000 | Callister et al. | |
| 6,113,607 A | 9/2000 | Lau et al. | |
| 6,145,505 A | 11/2000 | Nikolchev et al. | |
| 6,176,240 B1 | 1/2001 | Nikolchev et al. | |
| 6,270,495 B1 | 8/2001 | Palermo | |
| 6,432,116 B1 | 8/2002 | Callister et al. | |
| 6,526,979 B1 | 3/2003 | Nikolchev et al. | |
| 6,572,643 B1 * | 6/2003 | Gharibadeh | 623/1.11 |
| 6,599,296 B1 * | 7/2003 | Gillick et al. | 606/108 |
| 6,634,361 B1 | 10/2003 | Nikolchev et al. | |
| 6,669,716 B1 * | 12/2003 | Gilson et al. | 623/1.11 |
| 6,679,266 B2 | 1/2004 | Nikolchev et al. | |
| 6,684,884 B2 | 2/2004 | Nikolchev et al. | |
| 6,705,323 B1 | 3/2004 | Nikolchev et al. | |
| 6,709,667 B1 | 3/2004 | Lowe et al. | |
| 6,763,833 B1 | 7/2004 | Khera et al. | |
| 6,871,650 B1 | 3/2005 | Nikolchev et al. | |
| 2001/0041900 A1 | 11/2001 | Callister et al. | |
| 2002/0020417 A1 | 2/2002 | Nikolchev et al. | |
| 2002/0029051 A1 | 3/2002 | Callister et al. | |
| 2002/0151958 A1 * | 10/2002 | Chuter | 623/1.13 |
| 2003/0029457 A1 | 2/2003 | Callister et al. | |
| 2003/0066533 A1 | 4/2003 | Loy | |
| 2004/0079377 A1 | 4/2004 | Nikolchev et al. | |
| 2004/0127918 A1 | 7/2004 | Nikolchev et al. | |
| 2004/0159324 A1 | 8/2004 | Nikolchev et al. | |
| 2004/0163650 A1 | 8/2004 | Lowe et al. | |
| 2004/0163651 A1 | 8/2004 | Nikolchev et al. | |
| 2004/0206358 A1 | 10/2004 | Nikolchev et al. | |
| 2004/0211429 A1 | 10/2004 | Nikolchev et al. | |
| 2005/0027305 A1 * | 2/2005 | Shiu et al. | 606/108 |
| 2005/0222665 A1 * | 10/2005 | Aranyi | 623/1.11 |
| 2006/0212107 A1 * | 9/2006 | Case et al. | 623/1.11 |

FOREIGN PATENT DOCUMENTS

| | | |
|---|---|---|
| EP | 0105669 | 4/1984 |
| WO | WO 94/24944 | 11/1994 |
| WO | WO 94/26175 | 11/1994 |
| WO | WO 96/40024 | 12/1996 |
| WO | WO 97/27893 | 8/1997 |
| WO | WO 98/26737 | 6/1998 |
| WO | WO 99/15116 | 4/1999 |
| WO | WO 01/13833 | 3/2001 |
| WO | WO 2008/064280 | 5/2008 |

OTHER PUBLICATIONS

T. Schmitz-Rode, MD, et al., "Experimental Nonsurgical Female Sterilization; Transcervical Implantation of Microspindles in Fallopian Tubes," Journal of Vascular and Interventional Radiology, vol. 5 (No. 6), p. 905-910 (Nov.-Dec. 1994).

T. Schmitz-Rode, MD, et al., "Self-Expandable Spindle for Transcatheter Vascular Occlusion; In Vivo Experiments," Radiology, vol. 188 (No. 1), p. 95-100 (Jul. 1993).

Erich E. Brueschke, M.D., et al., "A Steerable Hysteroscope and Mechanical Tubal Occlusive Devices," Advances in Female Sterilization Techniques, Medical Department, Harper & Row, Hagerstown, MD, p. 182-196, (1976).

* cited by examiner

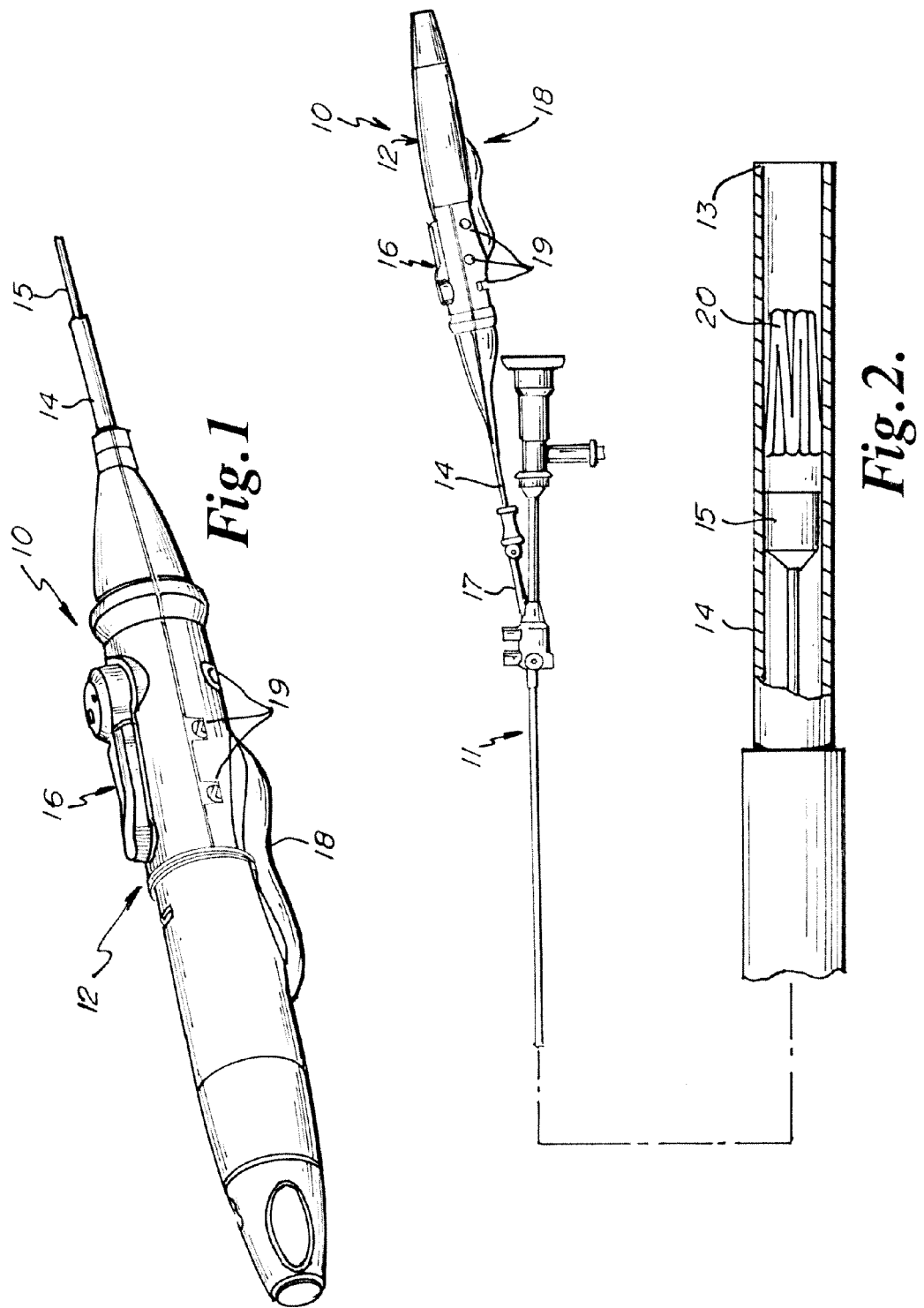

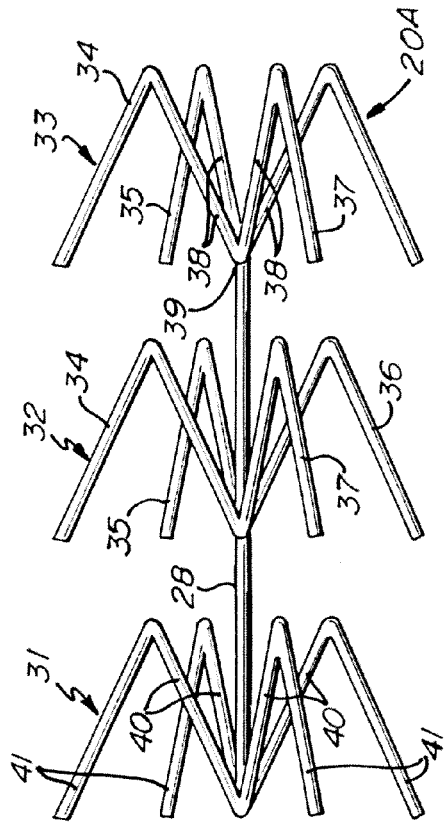
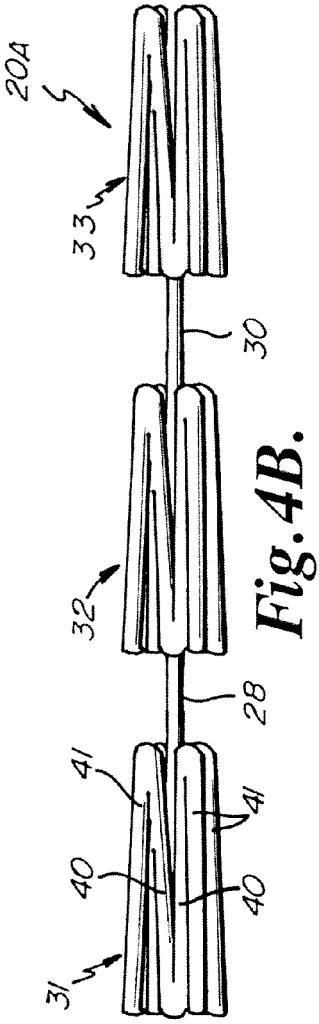
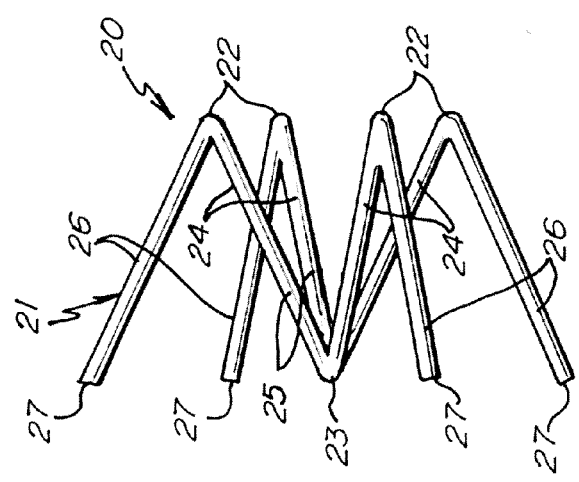
Fig. 4A.
Fig. 4B.
Fig. 3.

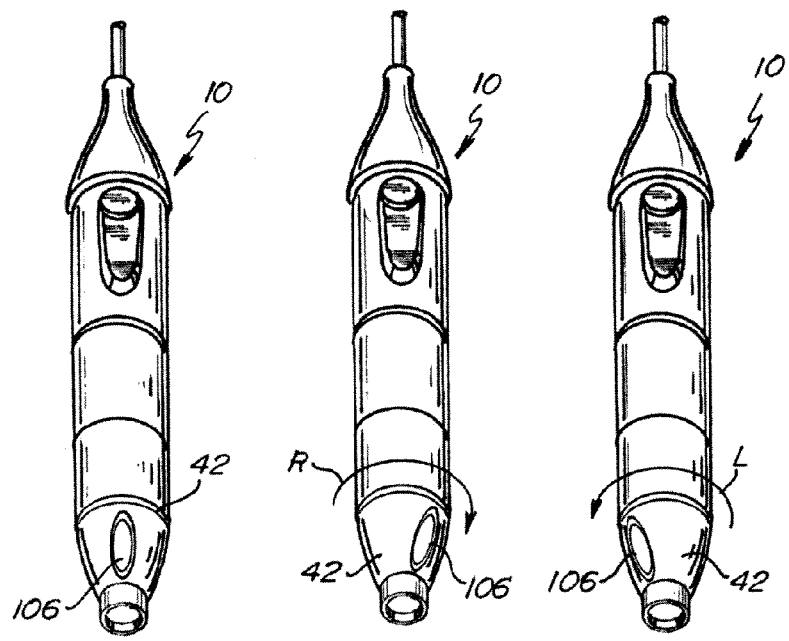
*Fig.9A.*  *Fig.9B.*  *Fig.9C.*
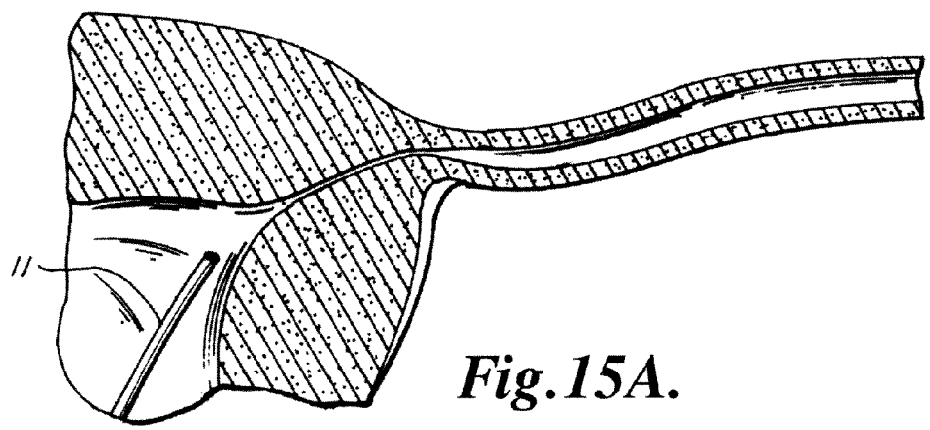
*Fig.15A.*

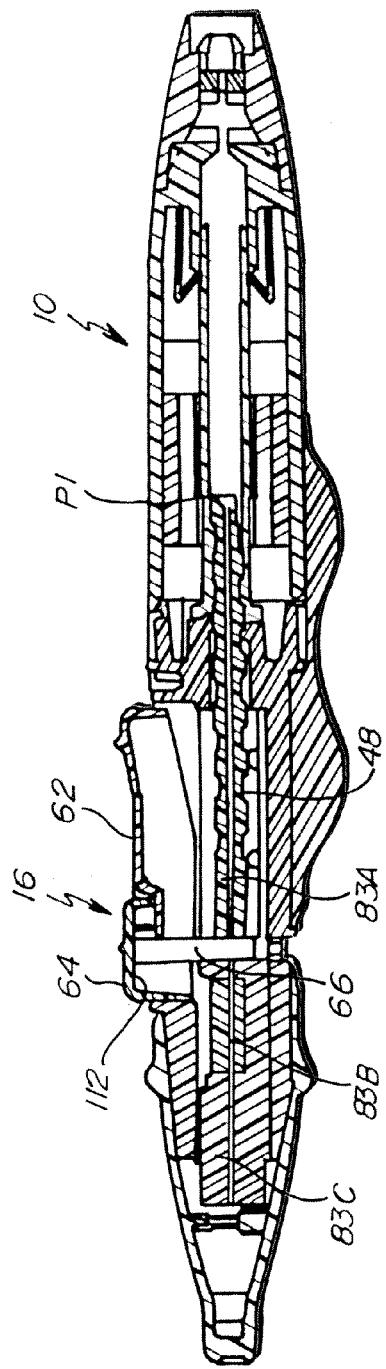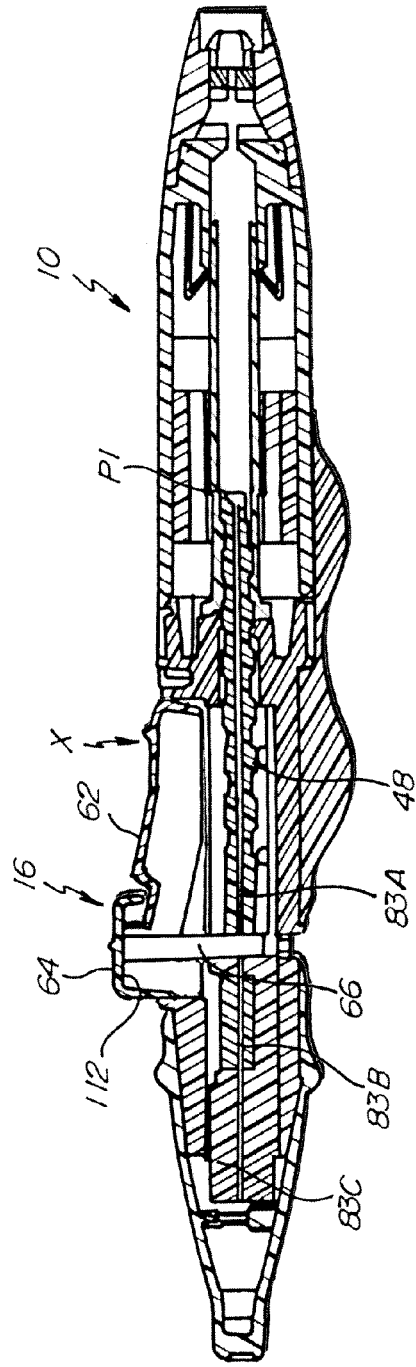

LINEAR MOTION DELIVERY SYSTEM FOR FEMALE STERILIZATION DEVICE

CROSS REFERENCE TO RELATED APPLICATIONS

This application claims the benefit of U.S. Provisional Application Ser. No. 60/744,178, filed Apr. 3, 2006, the entirety of which is hereby incorporated by reference.

BACKGROUND OF THE INVENTION

This present invention generally relates to a delivery system for a device to occlude body lumens. The invention is particularly useful for delivering occlusion devices to reproductive lumens, such as a female patient's fallopian tubes or a male patient's vas deferens, to affect contraception and/or sterilization.

Conventional contraceptive strategies generally fall within three categories: physical barriers, drugs, and surgery. While each have certain advantages, they also suffer from various drawbacks. Barriers such as condoms and diaphragms are subject to failure due to breakage, displacement, and misplacement. Drug strategies, such as the pill and Norplant™, which rely on artificially controlling hormone levels, suffer from known and unknown side-effects from prolonged use. Surgical procedures, such as tubal ligation and vasectomy, are very effective, but involve the costs and attendant risks of surgery, and are frequently not reversible.

In recent years, stent-like occlusion devices have been developed that may be inserted into a fallopian tube through a catheter coupled to an occlusion device delivery system. This type of minimally invasive procedure eliminates the risks associated with surgery, and therefore, is much more desirable to many patients. One such example of an occlusion device and corresponding delivery system is described in U.S. Patent Application Publication 2005/0085844 to Tremulis et al. Once deployed within the fallopian tube, the stent-like occlusion device expands and contacts the inner walls of the tube. Over time, fallopian tube tissue grows into the occlusion device, thereby forming a barrier within the fallopian tube. Tissue growth may be accelerated by incorporating growth hormones into the occlusion device. As one skilled in the art will appreciate, in order for the occlusion device to form a reliable contraceptive barrier, it must be deployed at a specific location within the fallopian tube. Thus, delivery systems that are easy to operate and improve the accuracy of occlusion device deployment within the fallopian tubes are desirable.

BRIEF SUMMARY OF THE INVENTION

The present invention provides a delivery system for deploying an occlusion device comprising a piston having a threaded proximal end, an elongated delivery catheter including a proximal end, a distal end, and an inner lumen extending between the proximal and distal ends of the delivery catheter, and a drive mechanism comprising an internally threaded nut member and a spring member. The piston, which is coupled at a distal end to the proximal end of the delivery catheter, is moveable between a first axial position and a second axial position. The internally threaded nut member is configured to receive the threaded proximal end of the piston. The spring member, which is coupled to the internally threaded nut member, is configured to rotate the nut member to drive the piston from the first axial position toward the nut member to the second axial position. Driving the piston toward the nut member retracts the attached delivery catheter and deploys an occlusion device from within the inner lumen and through the distal end of the delivery catheter.

The delivery system may also include a triggering mechanism configured to control axial movement of the piston. The triggering mechanism may be designed such that the piston may be driven toward the nut member only upon actuation of the triggering mechanism.

BRIEF DESCRIPTION OF THE DRAWINGS

FIG. 1 is a perspective view of a delivery system for an occlusion device in accordance with the present invention.

FIG. 2 is a side view of the delivery system of FIG. 1 inserted into a hysteroscope.

FIG. 3 illustrates one embodiment of an occlusion device that may be deployed using the delivery system of FIG. 1.

FIG. 4A illustrates an alternative embodiment of an occlusion device that may be deployed using the delivery system of FIG. 1.

FIG. 4B illustrates the occlusion device of FIG. 4A in a constricted configuration.

FIGS. 9A-9C illustrate the operation of a safety indicator attachable to a proximal end of the delivery system.

FIGS. 10A and 10B illustrate the positions of the delivery system drive mechanism and a delivery system triggering mechanism prior to deployment of an occlusion device.

FIGS. 11A-12B illustrate the positions of the delivery system drive mechanism and the delivery system triggering mechanism during deployment of a first occlusion device.

FIGS. 15A-15C illustrate a method for deploying an occlusion device into a fallopian tube in accordance with the present invention.

DETAILED DESCRIPTION OF THE INVENTION

Figure 5:
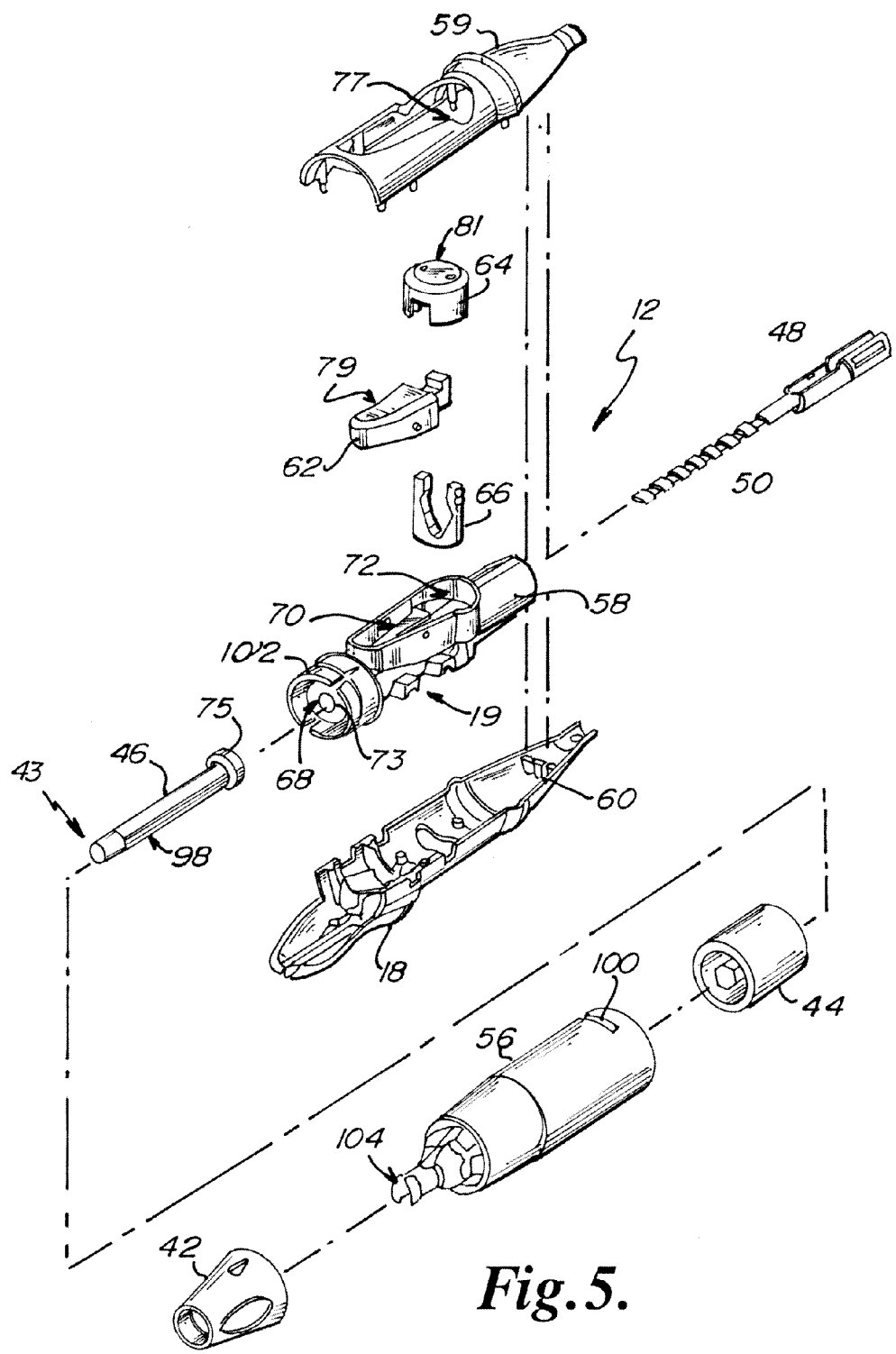
FIG. 5 is an exploded perspective view of the delivery system of FIG. 1.

FIG. 1 is a perspective view of delivery system 10 for an occlusion device according to the present invention, which generally includes housing 12, elongated delivery catheter 14, stabilizer wire 15, triggering mechanism 16, ergonomic grip 18, and deployment indicators 19. Delivery system 10 is designed to be used together with a hysteroscope, as shown in FIG. 2, to access a body lumen of a patient for the purpose of delivering and deploying an occlusion device in order to occlude the body lumen. Although delivery system 10 may be useful to deliver an occlusion device to various types of body lumens, the invention will hereinafter be described with reference to a system for delivering an occlusion device to a patient's fallopian tube. However, one skilled in the art will appreciate that delivery system 10 may also be used to occlude numerous other body lumens such as, for example, a vein, an artery, or the vas deferens. Thus, reference is made to the fallopian tube for purposes of example and not for limitation.

Delivery system 10 may provide for the delivery of one or more occlusion devices. If more than one occlusion device is to be delivered within the body, there is no need to remove delivery catheter 14 to deliver the additional devices. In this scenario, the physician may deliver one device to the first of two fallopian tubes, and subsequently access the other fallopian tube with delivery catheter 14 without removing the catheter. The use of more than one occlusion device has the advantage of speeding the overall procedure time and reducing overall costs for the procedure because only one delivery catheter 14 is required. For purposes of explanation, it will be assumed that delivery system 10 is designed for delivery of up to two occlusion devices. However, embodiments of delivery system 10 that are designed for delivery of any number of occlusion devices are contemplated.

To begin an occlusion procedure, hysteroscope 11 is inserted through the patient's vagina and into the uterus such that a distal end of hysteroscope 11 is positioned near the opening of a fallopian tube. As shown in FIG. 2, delivery catheter 14 is then inserted into working port 17 of hysteroscope 11 and fed through a working port lumen until distal end 13 of delivery catheter 14 is properly positioned within the fallopian tube. The physician then preferably grasps housing 12 such that the physician's thumb rests on triggering mechanism 16 and one or more fingers engage ergonomic grip 18. The physician then actuates triggering mechanism 16, thereby retracting delivery catheter 14 with respect to stabilizer wire 15, which is held in a stationary position by a crimp sleeve within housing 12. The relative movement of delivery catheter 14 with respect to the stationary stabilizer wire 15 results in occlusion device 20 being deployed through distal end 13 of catheter 14. Deployment of the occlusion device may be confirmed by the physician via deployment indicators 19 as will be discussed in more detail to follow.

FIG. 3 illustrates one embodiment of an occlusion device 20 that may be used with delivery system 10 and which is suitable to occlude a patient's reproductive lumen, such as a fallopian tube. Occlusion device 20 is in the form of a spider segment 21 having a plurality of expansive elements 22 which radiate from central location 23. The expansive elements have first sections 24 with first ends 25 secured to central location 23 and second sections 26 with free ends 27 radially displaced from central location 23 in the expanded configuration as shown. Central location 23 need not be the geometric center of device 20. For example, it may be offset from the geometric center and be provided with expansive elements of different lengths.

FIG. 4A represents an elevational view of an alternative occlusion device 20A with multiple spider segments 31, 32 and 33 that have the same structure as spider segment 21 shown in FIG. 3. In particular, occlusion device 20A has three spider segments, although occlusion devices having any number of spider segments are possible. The individual spider segments 31-33 have expansive elements 34, 35, 36 and 37 which are secured by first ends 38 to the central location 39 and are configured to engage the interior body lumen and seat the occlusion device therein. Each expansive element has a first section 40 adjacent to the central location or center line axis 39 and oriented toward one end of occlusion device 20A, and a second section 41 oriented toward the other end of the occlusion device. The angle between first and second sections 40 and 41 of the expansive elements ranges from about 20 degrees to about 75 degrees, preferably from about 30 degrees to about 60 degrees. Spider segments 31 and 32 are interconnected by beam 28 and spider segments 32 and 33 are interconnected by beam 30, both of which lie along center line axis 39.

While FIG. 4A illustrates occlusion device 20A in an expanded configuration, FIG. 4B illustrates device 20A compressed into a constricted configuration with first and second sections 40 and 41 of expansive elements 34-37 folded together so as to present a smaller profile.

Occlusion devices 20 and 20A may be formed from any suitable material, such as Nitinol. Furthermore, the inner surfaces of the occlusion devices preferably contain a tissue growth support member, such as polyethylene terephthalate (PET) fibers, that stimulates an inflammatory tissue response, which in combination with benign fibrous in-growth, provides fallopian tube occlusion. The combination of radial expansion and tissue in-growth contribute to the anchoring effect of the occlusion device.

One skilled in the art will appreciate that occlusion devices 20 and 20A are merely two examples of occlusion devices that may be used with delivery system 10 to occlude a lumen within the patient's body. Thus, delivery system 10 may be used with numerous other types of occlusion devices without departing from the intended scope of the present invention.

The components of delivery system 10 will now be described in further detail with reference to FIG. 5, which is an exploded view of delivery system 10. As illustrated in FIG. 5, in addition to the components shown in FIG. 1, delivery system 10 also includes safety indicator 42, drive mechanism 43 formed from power spring 44 and nut 46, and piston 48 having threaded portion 50. Housing 12 includes handle 56, main body portion 58, first outer shell 59, and second outer shell 60. Triggering mechanism 16 includes actuation button 62, deployment button 64, and gate 66.

Housing 12 houses the components of delivery system 10. Main body portion 58 of housing 12 contains bore 68 for piston 48, nest 70 for actuation and deployment buttons 62 and 64, pocket 72 for gate 66, and mating clutch face 73 configured to mate with distal end 75 of nut 46 when delivery system 10 is assembled.

First and second outer shells 59 and 60 are designed to snap together to enclose main body 58 as illustrated in FIG. 1. First outer shell 59 is designed with an opening 77 to allow actuation and deployment buttons 62 and 64 to protrude through housing 12 so that they can be actuated by the physician during an occlusion procedure. Second outer shell 60 includes ergonomic grip 18 protruding from an outer surface of the shell preferably at a location opposite that of triggering mechanism 16. In particular, ergonomic grip 18 is contoured so as to provide a secure, comfortable grip for one or more of the physician's fingers while also providing a reference to the physician as to the position of housing 12 in relation to their hand. Ergonomic grip 18 may be formed integral with housing 12 or as a separate component that may be attached to housing 12 during assembly, such as by a snap-fit feature, an adhesive, or numerous other methods as will be appreciated by one skilled in the art.

Actuation button 62 includes thumb locator means 79, while deployment button 64 includes thumb locator means 81. As shown in FIG. 5, thumb locator means 79 includes a single "bump" protruding from actuation button 62, while thumb locator means 81 includes a pair of "bumps" protruding from deployment button 64. It may be preferable to have a different number of "bumps" on each button to assist the physician with differentiating between the buttons without actually viewing them. Actuation button 62 and deployment button 64 may also be designed with an ergonomic contour which, when combined with thumb locator means 79 and 81, allows the physician to easily and blindly operate triggering mechanism 16 to deploy an occlusion device.

Gate 66 is positionable within pocket 72 of housing main body 58, and functions to control the movement of piston 48 within the main body. As will be discussed in more detail in subsequent paragraphs, gate 66 serves multiple functions including but not limited to providing: an audible snap when delivery system 10 is "armed" (i.e., when actuation button 62 has been actuated); incremental travel of piston 48; and a common interface between actuation button 62, deployment button 64, piston 48, and main body 56. Gate 66 operates in a controlled motion similar to that of a flood gate. Thus, as gate 66 moves in a radial direction with respect to housing 12 and "unblocks" the axial path required by piston 48, the piston is able to slide axially by a predetermined distance.

Figure 6:
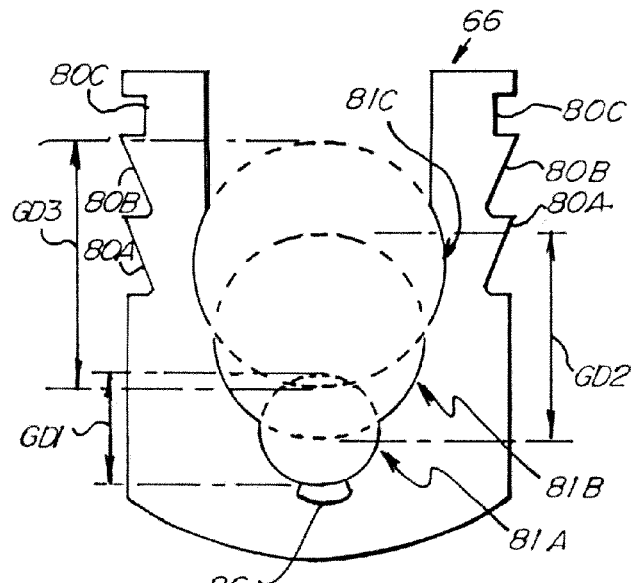
FIG. 6 is illustrates a gate member of the delivery system.

As further illustrated in FIG. 6, gate 66 includes first, second, and third pairs of ratcheting teeth 80A, 80B, and 80C, respectively. As will be discussed in more detail to follow, a deployment button flange is designed to mate with first pair of ratcheting teeth 80A prior to deploying either of the two occlusion devices. The deployment button flange is designed to mate with second pair of ratcheting teeth 80B during deployment of the first occlusion device. Finally, the deployment button flange is designed to mate with third pair of ratcheting teeth 80C during deployment of the second occlusion device. An inner portion of gate 66 includes a first circular region 81A having a diameter GD1, a second circular region 81B having a diameter GD2, and a third circular region 81C having a diameter GD3. Gate diameters GD1-GD3 correspond with piston diameters PD1-PD3 (as will be discussed in reference to FIG. 7A) in order to control the incremental movement of piston 48 within housing 12.

Figure 7A:
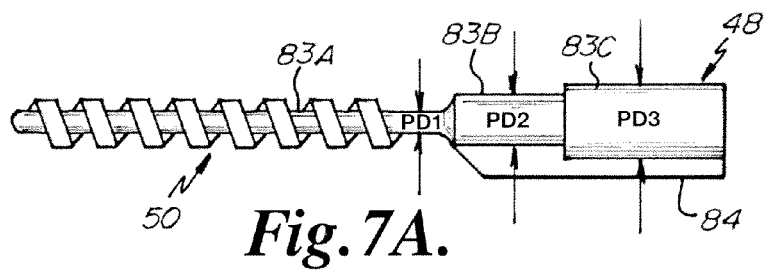
FIG. 7A is a side view of a piston of the delivery system.
Figure 7B:
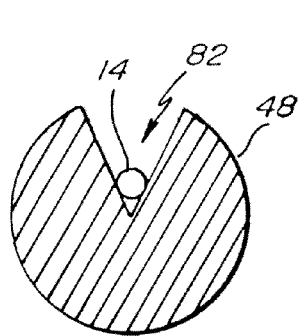
FIG. 7B is a cross-sectional view of the piston of FIG. 7A.

FIGS. 7A and 7B are side and cross-sectional views, respectively, of piston 48. Piston 48 is driven by drive mechanism 43 during deployment of an occlusion device in order to retract a predetermined length of delivery catheter 14 back into housing 12. In particular, piston 48 is designed to mate with nut 46 of drive mechanism 43 on a proximal end and with delivery catheter 14 on a distal end. As illustrated in FIG. 7B, piston 48 includes slot 82 designed to receive delivery catheter 14, which is preferably bonded into the slot with a suitable adhesive.

Threaded portion 50 of piston 48 is an important feature of delivery system 10. In particular, threaded portion 50 is designed to mate with a complementary threaded interior region of nut 46 (which is driven by power spring 44) in order to provide the system with the required linear motion to retract delivery catheter 14 and deploy the occlusion devices. The pitch of threaded portion 50, along with integrated friction plates on nut 46 and main body 58, control the deployment speed and the maximum force (tensile) applied to delivery catheter 14. In one embodiment, the thread design on threaded portion 50 of piston 48 may be a modified buttress design, which may provide an optimal drive face (90 degrees to axis) as well as a sufficient amount of thread line in order to modify the speed of deployment.

As illustrated in FIG. 7A, piston 48 includes a first section 83A having a first diameter PD1, a second section 83B having a second diameter PD2, a third section 83B having a third diameter PD3, and an axial key 84. Piston diameters PD1-PD3 correspond with gate diameters GD1-GD3 described above. In one embodiment, each gate diameter is slightly larger than its corresponding piston diameter. Prior to any actuation of actuation or deployment buttons 62 and 64, first section 83A of piston 48 is in axial alignment with first circular region 81A of gate 66. When gate 66 is repositioned through a first actuation of actuation and deployment buttons 62 and 64, second section 83B of piston 48 is in axial alignment with second circular region 81B of gate 66, and piston 48 is driven proximally into nut 46 of driving mechanism 43. Similarly, when gate 66 is repositioned through a second actuation of actuation and deployment buttons 62 and 64, third section 83C of piston 48 is in axial alignment with third circular region 81C of gate 66, and piston 48 is driven even further into nut 46.

Axial key 84 of piston 48 is designed to slide within axial slot 86 in gate 66 as well as a similar axial slot on an inner surface of main body 58 of housing 12. Axial key 84 prevents piston 48 from rotating when power spring 44 (through nut 46) provides a torque on the piston. Without a feature such as axial key 84, piston 48 would spin within housing 12 and therefore would not be able to supply the required linear motion to retract delivery catheter 14 and deploy the occlusion devices.

Figure 8:
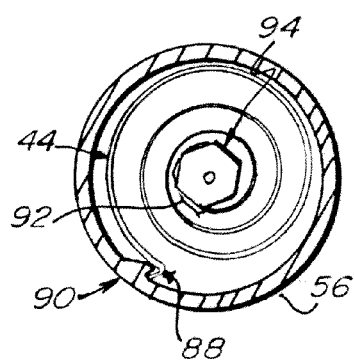
FIG. 8 illustrates a portion of a delivery system drive mechanism in accordance with the present invention.

As disclosed previously, drive mechanism 43 includes power spring 44 and nut 46, and serves as the "motor" of delivery system 10 to allow deployment of occlusion devices from delivery catheter 14. As illustrated in the cross-sectional view of FIG. 8, which depicts power spring 44 within handle portion 56 of housing 12, the power spring is formed from a plurality of coils of a metal strip material designed to be housed within the handle. In particular, power spring 44 includes first end 88 attached to dovetail slot 90 formed in an inner surface of handle 56. A second end 92 of power spring 44 forms an expandable hex portion 94 configured to mate with and receive nut 46.

Nut 46 mates with threaded portion 50 of piston 48 to drive the piston and the attached delivery catheter 14 proximally in order to deploy an occlusion device from within the catheter. In particular, nut 46 serves as the interface between piston 48 and power spring 44. Nut 46 includes a hex-shaped drive surface 98 that mates with expandable hex portion 94 of power spring 44 to create a slidable connection therebetween and allow power spring 44 to torque nut 46 and thus, drive piston 48 to retract delivery catheter 14 as discussed above.

As best seen in FIG. 1, when assembled handle 56 houses drive mechanism 43. A locking tab notch 100 in handle 56 is designed to receive locking tab 102 on main body 58 of housing 12 to lock handle 56 to the main body. Locking handle 56 to main body 58 also has the advantage of preventing the handle from counter-torquing after power spring 44 is torqued during assembly of delivery system 10.

It is desirable to use a constant force power spring with drive mechanism 43 in order to deliver each occlusion device with similar speeds and delivery forces. One skilled in the art will appreciate that other types of springs may be used, such as traditional compression springs. However, compression springs lose much of their stored power after the first deployment of an occlusion device, thus resulting in delivery speeds and forces that vary with each deployment. Another advantage of constant force power springs is that they provide a torque or twist feel during deployment rather than a kick forward or backward. This assists the physician with accurate placement of an occlusion device in a fallopian tube since any forward or backward movement of delivery system 10 during deployment may dramatically affect the location at which the occlusion device is deployed.

Safety indicator 42, which is attachable to snap feature 104 on the proximal end of handle 56, is a reference tool for the physician in order to indicate, for example, which fallopian tube the physician is occluding. In one embodiment, snap feature 104 may be designed as a rigid ratcheting system. A ratcheting-type system allows safety indicator 42 to ratchet in a twisting-type motion, thus giving tactile feedback to the physician. Operation of safety indicator 42 is illustrated in FIGS. 9A-9C. In particular, the physician may rotate safety indicator 42 such that an arrow marker 106 on the outer surface of the indicator moves between a "neutral" position (FIG. 9A), a "right side" position (FIG. 9B), and a "left side" position (FIG. 9C). Arrow marker 106 may be molded into safety indicator 42, or alternatively it may be printed on an outer surface of the indicator. Although safety indicator 42 is not a necessary component of the present invention, it may be included as a safety measure to provide the physician with a means of keeping track of which tube is being occluded in case the physician is interrupted during the occlusion procedure.

Prior to inserting delivery catheter 14 of delivery system 10 into the patient to begin the occlusion procedure, arrow marker 106 on safety indicator 42 will be in the "neutral position" as shown in FIG. 9A. When the physician begins the occlusion procedure of, for example, the right fallopian tube, safety indicator 42 is rotated such that arrow marker 106 is in the "right position" as shown by arrow R in FIG. 9B. Finally, before inserting delivery catheter 14 into the left fallopian tube to occlude that tube, the physician rotates safety indicator 42 such that arrow marker 106 is in the "left position" as shown by arrow L in FIG. 9C.

FIGS. 10A-14B illustrate the operation of triggering mechanism 16 and the associated linear movement of piston 48 and attached delivery catheter during an occlusion procedure. As will become apparent in the description of these figures, actuation button 62 and deployment button 64 function together to control movement of gate 66. In particular, actuation button 62, deployment button 64, and gate 66 function together to build-up the actuation and deployment forces required to deploy an occlusion device from delivery catheter 14.

Deployment of an occlusion device with delivery system 10 is accomplished by a simple two-step movement by the physician. The first step is actuating actuation button 62, which prepares the system for deployment of an occlusion device (by "arming" the system). The second step is actuating deployment button 64, which results in deployment of the device. It is not possible to actuate deployment button 64 without first actuating actuation button 62. As a result, a safety mechanism is created for preventing accidental deployment of the devices.

Figure 10A:
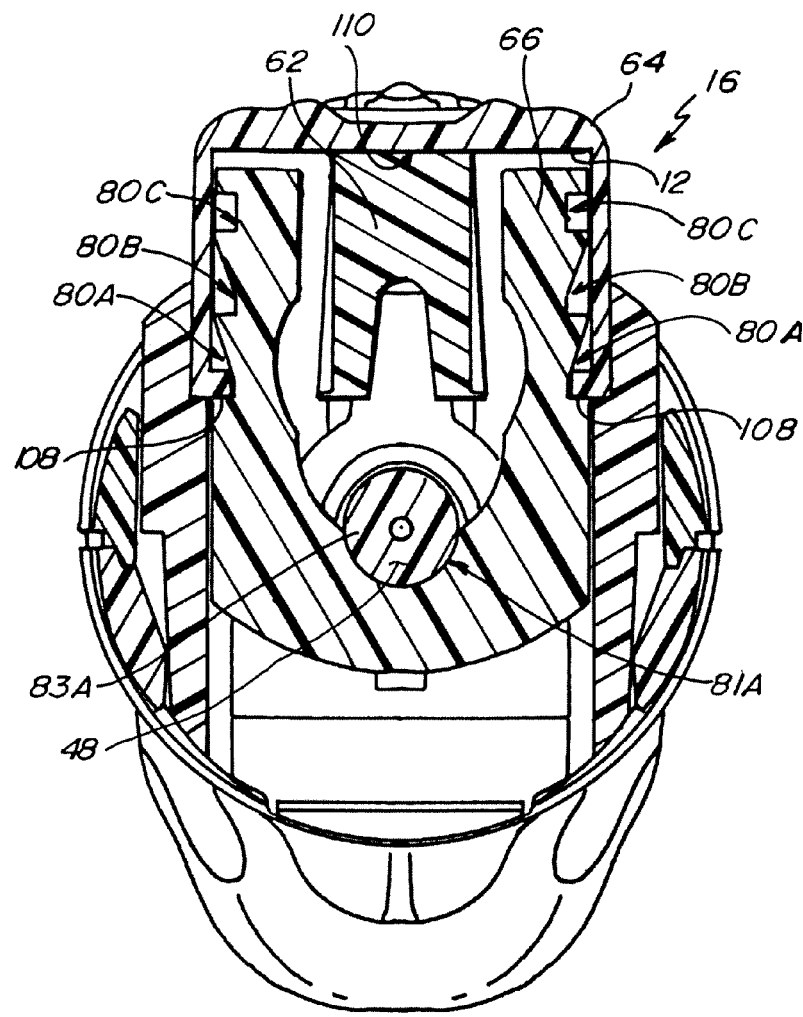

FIGS. 10A and 10B illustrate the position of gate 66 and piston 48 prior to deployment of either occlusion device (the "loaded" position). In particular, FIG. 10A is an end view of triggering mechanism 16 within housing 12, while FIG. 10B is a cross-sectional view of delivery system 10 illustrating the initial position of piston 48. As shown in FIG. 10A, deployment button 64 includes flange 108 configured to mate with first pair of ratcheting teeth 80A of gate 66. Tip portion 110 of actuation button 62 is designed to push against inner wall 112 of deployment button 64 when the deployment button is actuated in order to arm delivery system 10 for deployment of an occlusion device. As will become apparent in the following figures, this is accomplished by ratcheting flange 108 of deployment button 64 up from, for example, first pair of ratcheting teeth 80A to second pair of ratcheting teeth 80B.

As shown in FIGS. 10A and 10B, in the loaded position, first section 83A of piston 48 is in alignment with first circular region 81A of gate 66, and the proximal end of threaded portion 50 is located at a first proximal position P1 within nut 46. At this point, piston 48 is prevented from being driven in the proximal direction because second section 83B of piston 48 is obstructed by gate 66. In other words, second section 83B of piston 48 is not in axial alignment with second circular region 81B of gate 66.

Figure 11A:
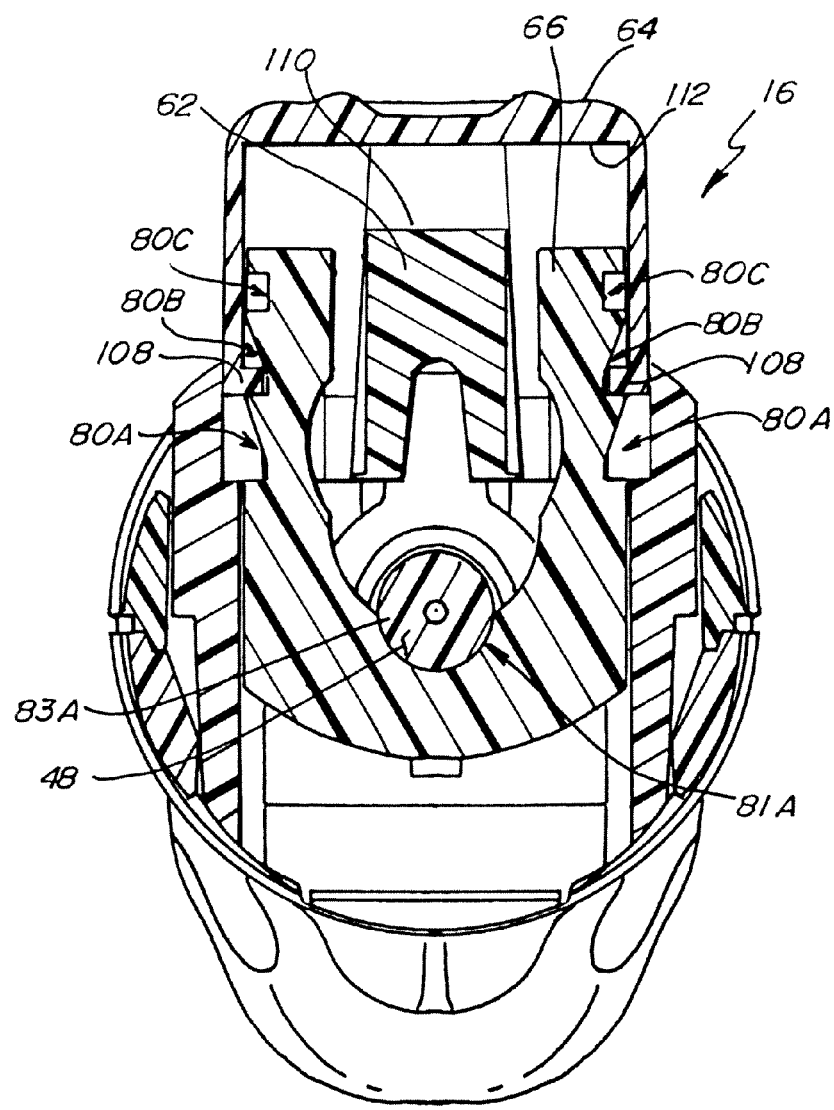
Figure 12A:
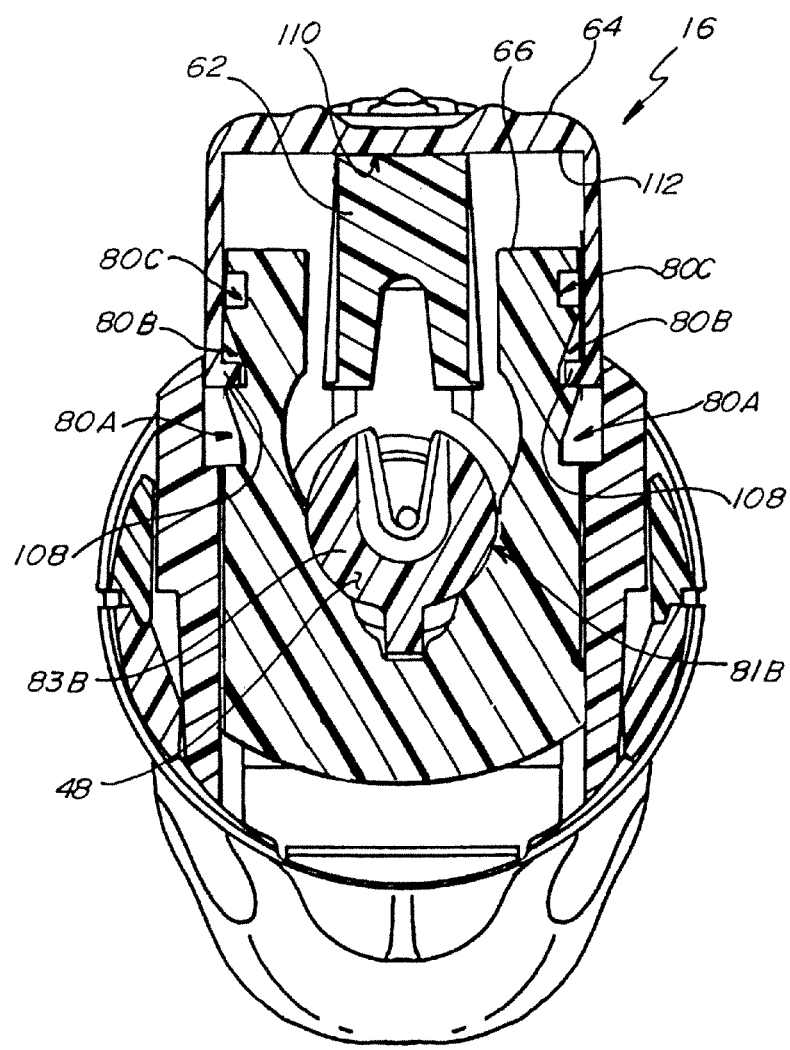
Figure 12B:
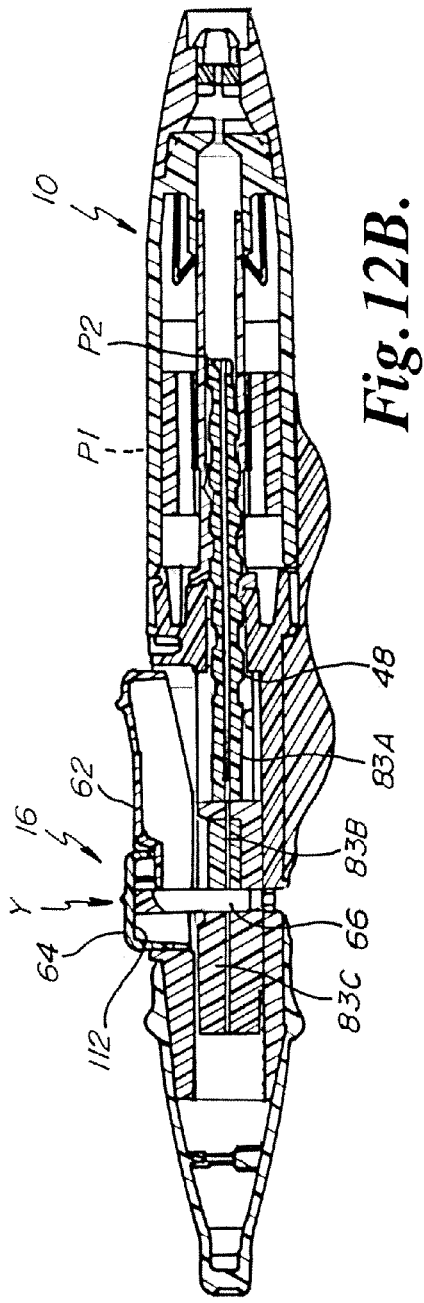

FIGS. 11A-12B illustrate the position of gate 66 and piston 48 during deployment of the first occlusion device. In particular, FIGS. 11A and 11B illustrate the position of gate 66 and piston 48 after the first step of actuating actuation button 62 to arm the system, while FIGS. 12A and 12B illustrate the position of gate 66 and piston 48 after the second step of actuating deployment button 64 to deploy the first occlusion device.

As shown in FIGS. 11A and 11B, actuating actuation button 62 in the direction indicated by arrow X causes tip portion 110 of actuation button 62 to push against inner wall 112 of deployment button 64. As a result, flange 108 of deployment button 64 ratchets up from first pair of ratcheting teeth 80A to second pair of ratcheting teeth 80B, thus arming delivery system 10 for deployment of the first occlusion device. The ratcheting movement results in an audible "click," which indicates to the physician that the system is now armed. At this point, gate 66 is still blocking piston 48 from being driven in the proximal direction by nut 46. Thus, piston 48 remains at the first proximal position P1 within nut 46.

As shown in FIGS. 12A and 12B, once delivery system 10 is armed, actuating deployment button 64 in the direction indicated by arrow Y causes gate 66 to move in a downward direction until second section 83B of piston 48 is in axial alignment with second circular region 81B of gate 66. As a result, power spring 44, via nut 46, drives piston 48 to the second proximal position P2 within nut 46, thus retracting delivery catheter 14 with respect to stabilizer wire 15 as discussed above to deploy the first occlusion device. At this point, piston 48 is prevented from being driven to a further proximal position because third section 83C of piston 48 is obstructed by gate 66. In other words, third section 83C of piston 48 is not in axial alignment with third circular region 81C of gate 66.

Figure 13B:
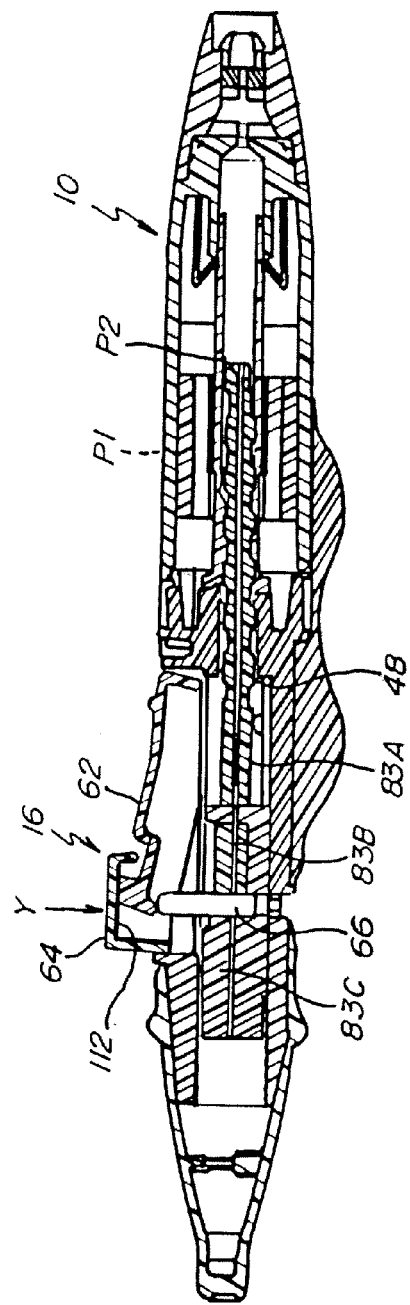
FIGS. 13A-14B illustrate the positions of the delivery system drive mechanism and the delivery system triggering mechanism during deployment of a second occlusion device.
Figure 13A:
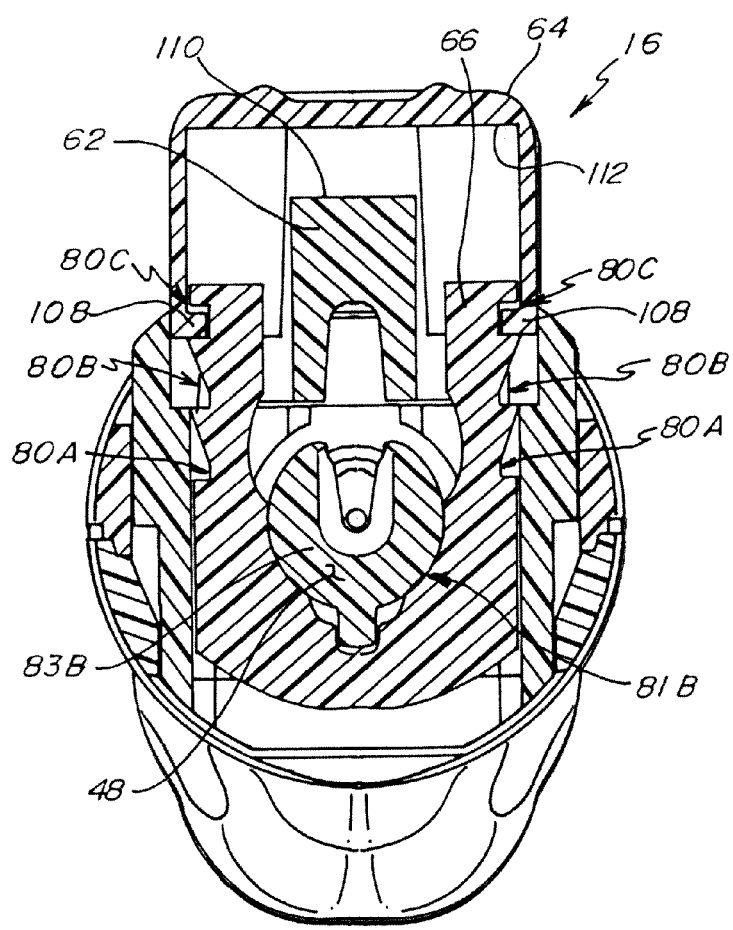
Figure 14A:
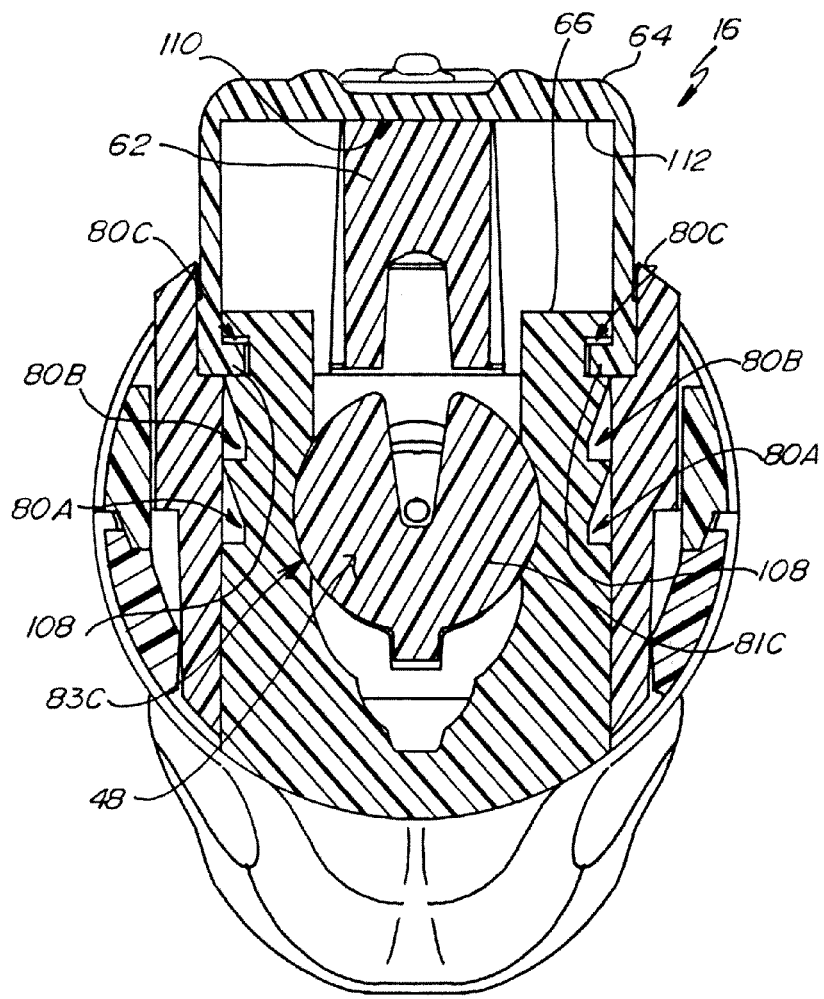
Figure 14B:
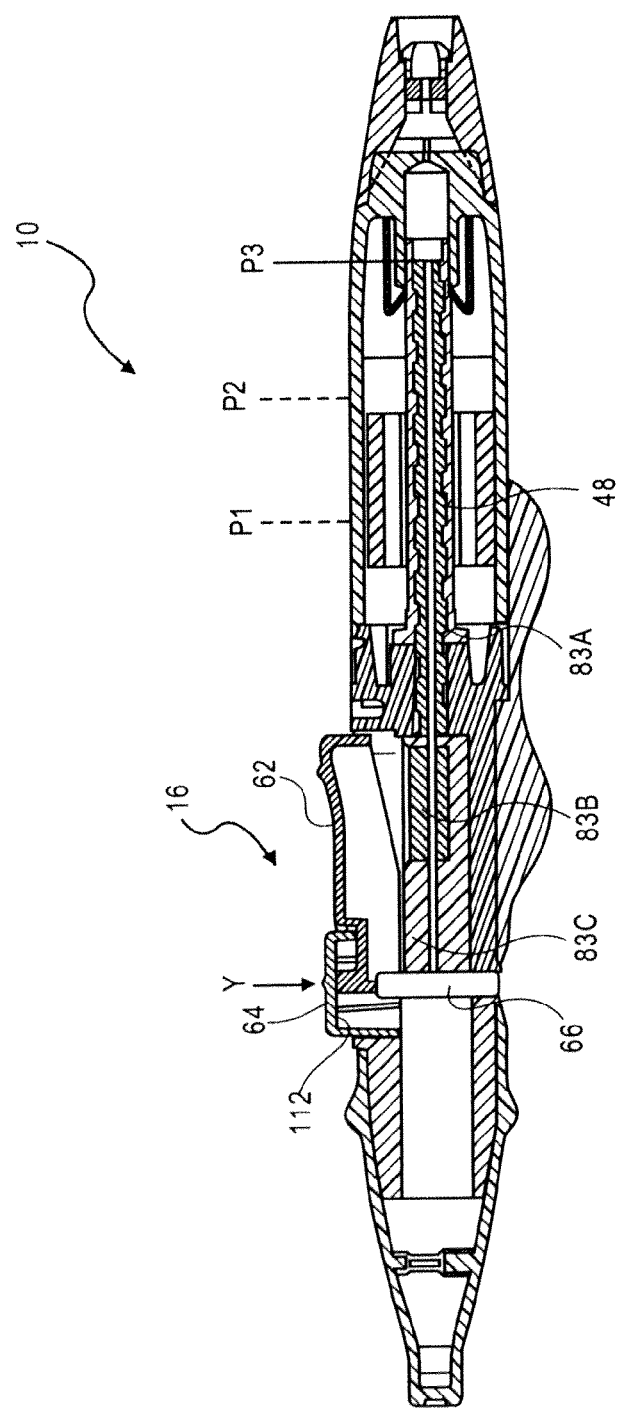

Finally, FIGS. 13A-14B illustrate the position of gate 66 and piston 48 during deployment of the second occlusion device. In particular, FIGS. 13A and 13B illustrate the position of gate 66 and piston 48 after the first step of actuating actuation button 62 to arm the system a second time, while FIGS. 14A and 14B illustrate the position of gate 66 and piston 48 after the second step of actuating deployment button 64 to deploy the second occlusion device.

As shown in FIGS. 13A and 13B, actuating actuation button 62 a second time in the direction indicated by arrow X causes tip portion 110 of actuation button 62 to push against inner wall 112 of deployment button 64. As a result, flange 108 of deployment button 64 ratchets up from second pair of ratcheting teeth 80B to third pair of ratcheting teeth 80C, thus arming delivery system 10 for deployment of the second occlusion device. The ratcheting movement results in an audible click, which indicates to the physician that the system is once again armed. At this point, gate 66 is still blocking piston 48 from being driven in the proximal direction by nut 46, and the piston remains at the second proximal position P2 within the nut.

As shown in FIGS. 14A and 14B, once delivery system 10 is armed, actuating deployment button 64 a second time in the direction indicated by arrow Y causes gate 66 to once again move in a downward direction until third section 83C of piston 48 is in axial alignment with third circular region 81C of gate 66. As a result, power spring 44 (via nut 46) drives piston 48 to the third and final proximal position P3 within nut 46, thus further retracting delivery catheter 14 with respect to stabilizer wire 15 to deploy the second occlusion device. At this point, both occlusion devices have been deployed and any further actuation of actuation button 62 or deployment button 64 will have no effect on the position of gate 66 or piston 48.

One skilled in the art will appreciate that the amount of force necessary to arm delivery system 10 is dependent upon many design characteristics, such as the the angle of the ratcheting teeth of gate 66. However, these design characteristics may be varied in order to achieve a desired level of required force. One skilled in the art will also appreciate the distance that flange 108 of deployment button 64 ratchets following each actuation of actuation button 62 may be constant, such as 0.100 inches per actuation, or may vary with each actuation.

Figure 15B:
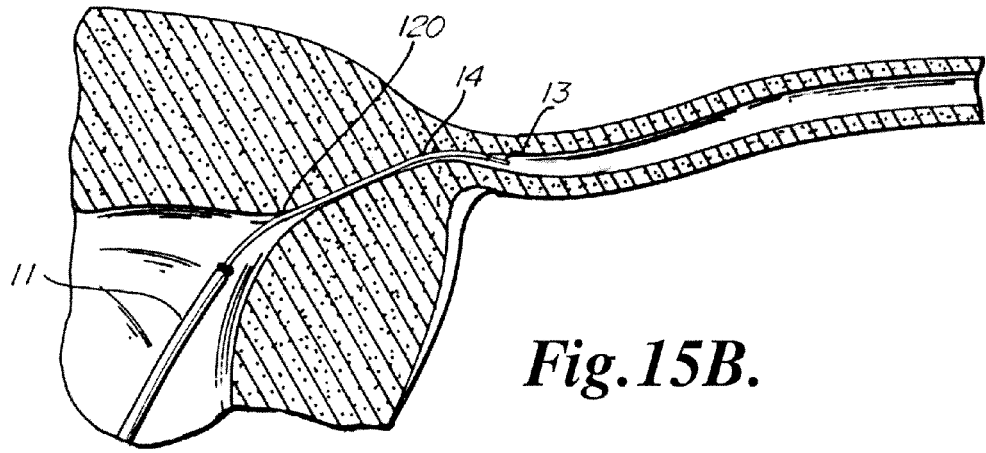

Now that the structure and operation of delivery system 10 has been described in detail, one example of a method of using the delivery system 10 to occlude a patient's fallopian tubes will be described. The physician begins the occlusion procedure by inserting a sterile flexible or rigid hysteroscope, such as hysteroscope 11 of FIG. 2, into the patient's uterine cavity through the cervix as shown in FIG. 15A. Next, the physician distends the uterine cavity using a physiologic saline infusion through the inflow channel of hysteroscope 11. Room temperature, or body temperature, saline is preferred in order to minimize fallopian tube spasm. The uterine anatomy and the tubal ostia are then identified and assessed through an imaging means as would be appreciated by one skilled in the art. The physician then determines whether the patient's left or right tube will be occluded first, and rotates safety indicator 42 to the position that corresponds to that tube. The process continues with the physician advancing delivery catheter 14 through the working channel of hysteroscope 11 while holding housing 12 until the distal tip of delivery catheter 14 extends into the uterus. The physician then positions distal tip 13 of delivery catheter 14 at the fallopian tube that will be occluded and aligns the catheter with the axial direction of the fallopian tube. As illustrated in FIG. 15B, delivery catheter 14 is then advanced into the fallopian tube using a slow, steady forward movement in order to prevent fallopian tube spasm until position marker 120 on delivery catheter 14 reaches the desired deployment position within the fallopian tube ostium.

Position marker 120 serves as an indication for the correct placement of the occlusion device within the fallopian tube. In one embodiment of position marker 120, a length of delivery catheter 14 near the distal end is colored a different color than the remainder of the catheter. As delivery catheter 14 is advanced through hysteroscope 11, the change in color on the distal end of delivery catheter 14 may be viewed through the hysteroscope as the distal end of the catheter enters the fallopian tube. When the colored position marker is completely located within the fallopian tube and disappears from view, the enclosed occlusion device is properly located at the desired depth and may be deployed within the fallopian tube. Depending on the length of position marker 120, the occlusion device may be located within the isthmic region of the fallopian tube, distal to the isthmic region, or even near the ampulla region of the fallopian tube.

In another embodiment, position marker 120 is a visual marker such as a line or geometric shape printed on delivery catheter 14. Alternatively, the visual marker may include raised portions or bumps that protrude from the outer surface of delivery catheter 14. As the visual marker enters the fallopian tube, the occlusion device is at the proper depth for deployment. Optionally, two markers may be used to show a pre-specified range of depths indicating proper placement of the occlusion device.

An alternative to visual means of placement is the use of ultrasound guidance. In this case, position marker 120 is echogenic and is positioned near the distal tip of delivery catheter 14. Optionally, a second marker may be used to locate the exact position of the occlusion device within delivery catheter 14.

Another means of placement for the occlusion device is under fluoroscopic guidance. In this case, position marker 120 may be a radiopaque marker located near the distal tip of delivery catheter 14. When the proper depth of delivery catheter 14 within the fallopian tube has been verified under fluoroscopy, the occlusion device is ready to be deployed. In addition, the occlusion device itself may be made radiopaque, either in part or in whole, allowing for direct visualization of the occlusion device under fluoroscopy.

Figure 15C:
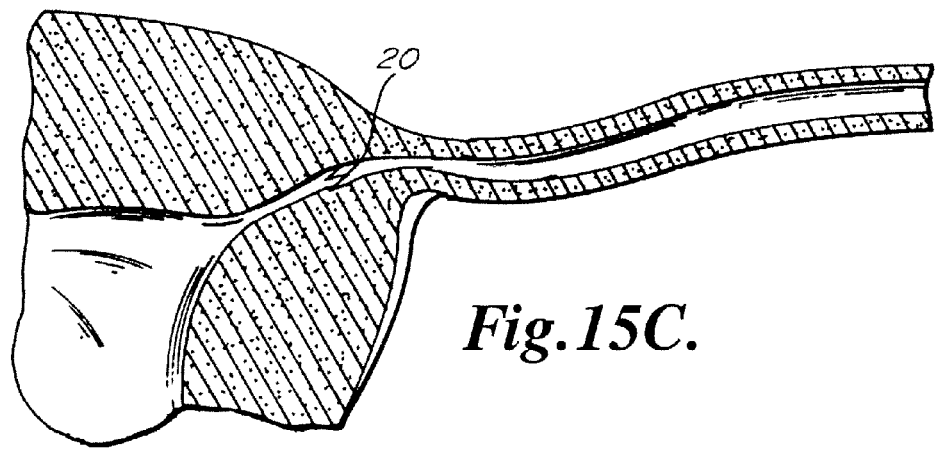

Following verification of the proper location of position marker 120 by any of the foregoing means, the physician then actuates actuation button 62, without moving housing 12 relative to hysteroscope 11, to arm delivery system 10 for deployment. As a result, deployment button 64 will elevate in preparation for device deployment. The physician may once again confirm proper depth of delivery catheter 14 using position marker 120 as a guide, and press deployment button 64 to deploy the occlusion device. In particular, this action retracts delivery catheter 14 while inner stabilizer wire 15 holds the occlusion device in the desired position within the fallopian tube. When the device is properly deployed, triggering mechanism 16 will make an audible and tactile click. At this point, the occlusion device will be deployed within the fallopian tube, as depicted by occlusion device 20 in FIG. 15C. Finally, the physician rotates safety indicator 42 to the position that corresponds to the second fallopian tube, and deploys a second occlusion device within the second tube following a process similar to that previous described.

Figure 16A:
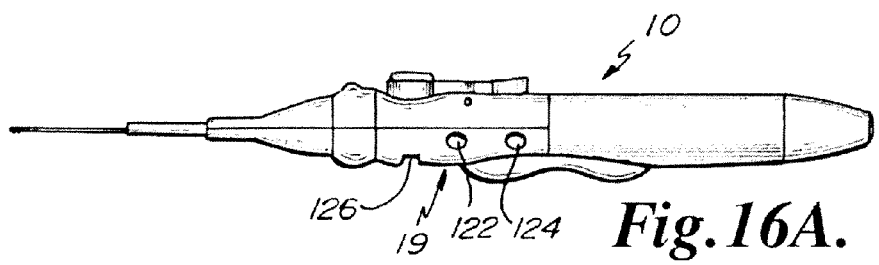
FIGS. 16A-16C illustrate a deployment indicator means for confirming deployment of the occlusion devices from the delivery system.
Figure 16B:
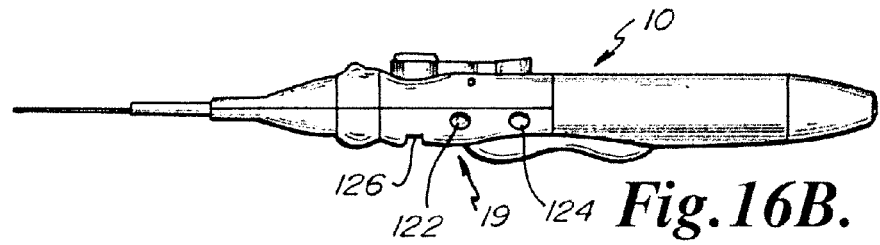
Figure 16C:
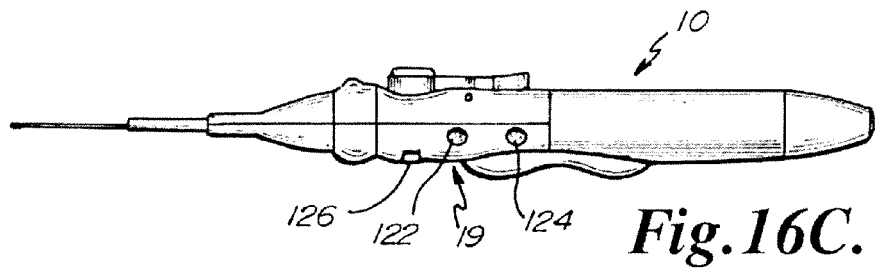

FIGS. 16A-16C illustrate the operation of deployment indicators 19 of delivery system 10. Deployment indicators 19 include first indicator window 122, second indicator window 124, and gate indicator 126. As shown in FIG. 16A, prior to deployment of the first occlusion device, neither first indicator window 122 nor second indicator window 124 are obstructed. Next, as shown in FIG. 16B, after deployment of the first occlusion device, piston 48 is driven proximally to proximal position P2 (illustrated in FIG. 12B) and is visible in first indicator window 122. Finally, as shown in FIG. 16C, after deployment of the second occlusion device, piston 48 is driven to an even further proximal position, proximal position P3 (illustrated in FIG. 14B), and is visible in second indicator window 124. Furthermore, gate 66 has moved radially downward such that it may now be felt by the physician in gate indicator 126. Thus, the physician may confirm deployment of the first and second occlusion devices by viewing first and second indicator windows 122 and 124 as well as by feeling gate 66 within gate indicator 126.

Although the present invention has been described with reference to preferred embodiments, workers skilled in the art will recognize that changes may be made in form and detail without departing from the spirit and scope of the invention.

What is claimed is:

1. A delivery system for deploying an occlusion device comprising:
   a piston assembly having a threaded proximal end, a distal end, an axial key, and being moveable between a first axial position and a second axial position;
   an elongated delivery catheter having a proximal end, a distal end, and an inner lumen extending between the proximal and distal ends of the delivery catheter, the proximal end of the delivery catheter coupled to the distal end of the piston assembly;
   a drive mechanism comprising: an internally threaded nut member configured to receive the threaded proximal end of the piston assembly, and a spring member coupled to the internally threaded nut member, the spring member configured to rotate the nut member to drive the piston assembly from the first axial position toward the nut member to the second axial position to retract the attached delivery catheter and deploy an occlusion device from within the inner lumen and through the distal end of the delivery catheter; and a gate member comprising an axial slot, and moveable between a first gate position and a second gate position upon actuation of a deployment button coupled to the gate member, wherein an outer dimension of the distal end of the piston assembly is larger than an outer dimension of the threaded proximal end of the piston assembly such that the piston assembly is maintained in the first axial position when the gate member is in the first gate position, and wherein the drive mechanism releases stored energy as a result of actuation of the gate member from the first gate position to the second gate position and causes the piston assembly to be driven to the second axial position while the axial key of the piston assembly slides within the axial slot of the gate member.

2. The delivery system of claim 1, wherein the piston assembly is driven toward the nut member when the gate member is in the second gate position.

3. The delivery system of claim 1, wherein the gate member is U-shaped.

4. The delivery system of claim 3, wherein movement of the gate member from the first gate position to the second gate position unblocks an axial path required to drive the piston assembly from the first axial position to the second axial position.

5. The delivery system of claim 1, further comprising an actuation button, and wherein the actuation button must be actuated prior to actuating the deployment button.

6. The delivery system of claim 1, wherein the gate member comprises a plurality of ratcheting teeth engageable with the deployment button.

7. The delivery system of claim 1, wherein the spring member is a power spring.

8. The delivery system of claim 1, further comprising one or more deployment indicators for confirming deployment of the occlusion device from within the inner lumen of the delivery catheter.

9. A minimally invasive system for occluding a body lumen of a patient, the system comprising:
- an elongated delivery catheter having a proximal end, a distal end, and an inner lumen extending between the proximal and distal ends of the delivery catheter;
- at least one self-expanding occlusion device disposed within the inner lumen of the delivery catheter, each occlusion device configured to expand when deployed within the patient's body lumen;
- a piston assembly having an axial key, a proximal end and a distal end, the distal end of the piston assembly coupled to the proximal end of the delivery catheter; and
- a drive mechanism coupled to the proximal end of the piston assembly, wherein the drive mechanism includes a spring member, and wherein the piston assembly and attached delivery catheter are driven toward the drive mechanism upon actuating a triggering mechanism to retract the delivery catheter and deploy the at least one self-expanding occlusion device through the distal end of the delivery catheter;
- wherein the triggering mechanism includes a gate member comprising an axial slot and being moveable between a first gate position and a second gate position upon actuation of a deployment button coupled to the gate member, wherein an outer dimension of the distal end of the piston assembly is larger than an outer dimension of the proximal end of the piston assembly such that the piston assembly is maintained in a first axial position when the gate member is in the first gate position, and wherein the drive mechanism releases stored energy as a result of actuation of the gate member from the first gate position to the second gate position and causes the piston assembly to be driven to a second axial position while the axial key of the piston assembly slides within the axial slot of the gate member.

10. The system of claim 9, wherein the drive mechanism comprises:
- a nut member configured to receive the proximal end of the piston assembly; and
- the spring member is operatively coupled to the nut member to rotate the nut member which drives the piston assembly from the first axial position toward the nut member to the second axial position.

11. The system of claim 10, wherein the gate member is U-shaped.

12. The system of claim 10, wherein the spring member is a power spring.

13. The delivery system of claim 9, wherein the triggering mechanism further comprises an actuation button, wherein the actuation button must be actuated prior to actuating the deployment button.

14. A minimally invasive system for occluding a body lumen of a patient, the system comprising:
- an elongated delivery catheter having a proximal end, a distal end, and an inner lumen extending between the proximal and distal ends of the delivery catheter;
- a self-expanding occlusion device disposed within the inner lumen of the delivery catheter, the occlusion device configured to expand when deployed within the patient's body lumen;
- a piston assembly having an axial key, a proximal end and a distal end, the distal end of the piston assembly coupled to the proximal end of the delivery catheter;
- a drive mechanism comprising: a rotatable nut member coupled to the proximal end of the piston assembly, and a torquing means comprising a spring member operatively coupled to rotate the nut member which drives the piston assembly and attached delivery catheter from a first axial position to a second axial position to retract the delivery catheter and deploy an occlusion device from within the inner lumen of the catheter; and
- a gate member comprising an axial slot, and moveable between a first gate position and a second gate position upon actuation of a deployment button coupled to the gate member, wherein an outer dimension of the distal end of the piston assembly is larger than an outer dimension of the proximal end of the piston assembly such that the piston assembly is maintained in the first axial position when the gate member is in the first gate position, and wherein the drive mechanism releases stored energy as a result of actuation of the gate member from the first gate position to the second gate position and causes the piston assembly to be driven to the second axial position while the axial key of the piston assembly slides within the axial slot of the gate member.

15. The system of claim 14, wherein the gate member is U-shaped.

16. The system of claim 15, wherein movement of the gate member from the first gate position to the second gate position unblocks an axial path required to drive the piston assembly from the first axial position to the second axial position.

17. The system of claim 14, wherein the spring is a power spring.

18. The system of claim 14, further comprising a deployment indicator for confirming deployment of the occlusion device from within the inner lumen of the delivery catheter.

19. A delivery system for deploying an occlusion device comprising:
- an elongated delivery catheter having a proximal end region, a distal end region, and an inner lumen extending between the proximal and distal ends of the delivery catheter;
- an occlusion device disposed within the inner lumen of the delivery catheter;
- a piston assembly having an axial key, a proximal end region and a distal end region, the distal end region of the piston assembly coupled to the proximal end region of the delivery catheter; and
- a drive mechanism coupled to the proximal end region of the piston assembly, wherein the drive mechanism includes a spring member, and wherein the piston assembly and attached delivery catheter are driven toward the drive mechanism upon actuating a triggering mechanism to retract the delivery catheter and deploy the occlusion device through the distal end of the delivery catheter;
- wherein the triggering mechanism includes a gate member comprising an axial slot and being moveable between a first gate position and a second gate position upon actuation of a deployment button coupled to the gate member, wherein an outer dimension of the distal end region of the piston assembly is larger than an outer dimension of the proximal end region of the piston assembly such that the piston assembly is maintained in a first axial position when the gate member is in the first gate position, and wherein the drive mechanism releases stored energy as a result of actuation of the gate member from the first gate position to the second gate position and causes the piston assembly to be driven to a second axial position while the axial key of the piston assembly slides within the axial slot of the gate member.

20. The system of claim 19, wherein the spring is a power spring.

21. The system of claim 19, wherein the gate member is U-shaped.

22. The system of claim 19, wherein movement of the gate member from the first gate position to the second gate position unblocks an axial path required to drive the piston assembly from the first axial position to the second axial position.

* * * * *

UNITED STATES PATENT AND TRADEMARK OFFICE
CERTIFICATE OF CORRECTION

| | | |
|---|---|---|
| PATENT NO. | : 8,562,628 B2 | Page 1 of 1 |
| APPLICATION NO. | : 11/695887 | |
| DATED | : October 22, 2013 | |
| INVENTOR(S) | : Mujwid et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1344 days.

Signed and Sealed this
Eleventh Day of August, 2015

Michelle K. Lee
*Director of the United States Patent and Trademark Office*